United States Patent
Sumén et al.

[11] Patent Number: 5,914,490
[45] Date of Patent: Jun. 22, 1999

[54] PROCEDURE FOR MEASURING THE COMPONENTS OF A COATING ON A MOVING BASE MATERIAL

[75] Inventors: Juha Antero Sumén, Kempele; Jouni Sakari Tornberg, Oulunsalo, both of Finland

[73] Assignee: Valmet Automatic, Inc., Helsinki, Finland

[21] Appl. No.: 08/909,287

[22] Filed: Aug. 11, 1997

[30] Foreign Application Priority Data

Feb. 13, 1997 [FI] Finland ................................. 970612

[51] Int. Cl.⁶ .......................... G01N 21/35; G01N 21/25
[52] U.S. Cl. .................................. 250/339.11; 250/359.1; 250/341.8
[58] Field of Search ........................ 250/359.1, 339.11, 250/339.12, 339.08, 341.8

[56] References Cited

U.S. PATENT DOCUMENTS

| | | | |
|---|---|---|---|
| 4,300,049 | 11/1981 | Sturm | 250/339.12 |
| 4,957,770 | 9/1990 | Howarth | 250/341.8 |
| 4,965,452 | 10/1990 | Sturm | 250/339.11 |
| 5,250,811 | 10/1993 | Lippert et al. | 250/359.1 |
| 5,338,361 | 8/1994 | Anderson et al. | |
| 5,455,422 | 10/1995 | Anderson et al. | |

FOREIGN PATENT DOCUMENTS

| | | |
|---|---|---|
| 0 272 645 | 6/1988 | European Pat. Off. . |
| 0 332 018 A3 | 9/1989 | European Pat. Off. . |
| 43 18 767 | 12/1994 | Germany .......... 250/339.11 |
| 2 127 541 | 4/1984 | United Kingdom . |

*Primary Examiner*—Constantine Hannaher
*Assistant Examiner*—Darren M. Jiron
*Attorney, Agent, or Firm*—Merchant, Gould, Smith, Edell, Welter & Schmidt, P.A.

[57] ABSTRACT

A procedure for measuring the components of the coating of paper via infrared measurement, the paper components being determined via a reflection measurement in the middle infrared range, e.g. by measuring the reflection peak using a wavelength of 2–12 μm.

13 Claims, 7 Drawing Sheets

PROCEDURE FOR MEASURING THE COMPONENTS OF A COATING ON A MOVING BASE MATERIAL

The present invention relates to a procedure for measuring the components of a coating on a moving base material by an infrared measuring technique.

The measurement of the amount of coating on coated paper is one of the most important paper quality measurements; in this description, 'paper' means conventional paper or cardboard.

The amount of coating has traditionally been measured (U.S. Pat. No. 5,338,361) continuously via absorption measurement in the near infrared (NIR) range. In IR range absorption measurement, the intensity of an IR beam absorbed by the coating or a quantity proportional thereto is measured as a function of the wavelength of the beam; the intensity of the beam absorbed by the coating as measured with the wavelength corresponding to the absorption peak of the component under measurement correlates with the amount of coating. The technique of measuring the components of paper coating via infrared measurement is in itself known in the art and will not be described here in detail.

The coating component to be measured is usually kaolin, which shows absorption peaks in the NIR range. However, NIR measurement is not adequate for measuring the other important coating component, calcium carbonate, because calcium carbonate shows no absorption peak in the NIR range. In this case, the total amount of coating can be calculated on the basis of kaolin measurement assuming that the ratio of the amounts of kaolin and calcium carbonate in the coating is constant. In reality, however, the ratio of the amounts of kaolin and calcium carbonate is not always constant, but the ratio may vary. Therefore, the prior-art method described above does not yield accurate results especially in the measurement of the amount of calcium carbonate. In addition, the method is only applicable when kaolin is used; when kaolin is not used as a coating component, the method cannot be applied at all.

Kaolin and calcium carbonate have more pronounced absorption peaks in the middle infrared (MIR) range than in the NIR range. Because of the intensive absorption and low scattering, absorption measurement in the MIR range can be assumed to be better suited for the measurement of the amounts of coating components than it is in the NIR range.

However, the measurement of coating components with MIR absorption is difficult to implement. If the measurement is performed by measuring through the paper, the fillers in the base paper will be included in the results. In addition, the paper may show such a high degree of absorption that measuring through the paper is impossible.

The object of the present invention is to eliminate the drawbacks described above.

A specific object of the invention is to present a new procedure for measuring the components of a coating on a moving base material using an infrared measuring technique in such a way that the measurement is better applicable especially for the determination of different coating components than prior-art measuring methods and so that the fillers in the base material do not cause problems in the measurement, A further object of the invention is to present a procedure for measuring the components of a coating on a moving base material, e.g. the components of the coating of paper, in such a way that the measurement is not disturbed by high absorption by the base material, e.g. paper.

As for the features characteristic of the invention, reference is made to the claims.

The invention is based on the unexpected fact discovered during investigations that a sharp increase in reflection was observed near the absorption peaks of the coating components under measurement. According to the hypothesis, the reflection should have been reduced in the absorption bands, in other words, the coating components should have absorbed light expressly in the areas of the characteristic absorption bands and absorption peaks of the components.

The procedure of the invention provides an accurate and practicable method for determining the components of the coating of paper using reflection measurement in an infrared range of 2.5–12 $\mu$m, preferably 5.5–11 $\mu$m, more preferably 6.2–10 $\mu$m. The procedure is particularly applicable for use in the measurement of the coating components of paper, i.e. e.g. in kaolin measurement with a wavelength of 8–11 $\mu$m, preferably 8.5–10 $\mu$m, and/or calcium carbonate measurement with a wavelength of 5.5–8 $\mu$m, preferably 6.2–7.3 $\mu$m. Generally, the measurement can be carried out using any wavelength in the middle infrared range, e.g. 2.5–12 $\mu$m.

The procedure of the invention is also applicable for the measurement of coating components on a moving base material on the surface of a roller in a roll coater or paper machine and/or in general on the surface of any metal plate.

Reflection measurement can be implemented using specular reflection measurement, in which the measuring beam is directed to the base material surface as an oblique beam of parallel rays and the parallel reflected beam reflected from the base material surface is detected by means of detectors, in other words, the intensity of the reflected beam is determined as a function of the wavelength.

In a particularly advantageous implementation of the invention, diffuse reflection is used, in which case a measuring beam is directed to the object under measurement and the intensity of the diffuse radiation reflected from the object in all directions is determined as a function of wavelength; the illumination of the object can also be implemented using diffused light.

Reflection measurement in the MIR range gives a very good correlation for the amounts of coating components, especially kaolin and carbonate and mixtures of these. The correlation is also very good for different kinds of base paper and/or cardboard in the calibration of the measurement of their coatings. The MIR range has several advantages as compared with the NIR range. In the MIR range, high absorption levels are obtained for all important coating components, and in addition the peaks are sharp and scattering is insignificant. Sharp peaks are a desirable feature in regard of the operation of measuring equipment based on interference filters, and the detectors and the low degree of scattering permits structural variations in the coating without detriment to calibration. The significance of the result is augmented by the tendency prevailing in the paper industry towards an increased use of carbonate-based coatings, which cannot be directly measured in the NIR range.

By applying the procedure of the invention it is possible to implement measuring devices which can be used for on-line measurement of the components of the coating of paper and/or cardboard in paper and coating machines, for on-line measurement of coatings on the rollers of paper coaters or paper machines or in general on metal plates, and also as tools for the inspection of paper and coating properties in laboratories. In particular, by applying the procedure of the invention, it is possible to implement a small-scale measuring device for the measurement of variations in the amount of coating for laboratory use by using optic equipment designed for small-scale measurement. In small-scale measurement, the measuring area may be of the order of 0.1–100 mm², preferably 0.1–10 mm², more preferably 0.1–2 mm², or even smaller than this. Naturally, the measuring area may also be larger, e.g. of the order of about 1 cm² (n=1–10 or larger), as is known in prior art. The total amount of coating under measurement, or in small-scale measurement the amount of coating to be measured, may vary e.g. between 3–40 g/m², preferably 17–25 g/m².

In the following, the invention is described in detail by the aid of embodiment examples by referring to the attached drawing, in which.

Figure 1:
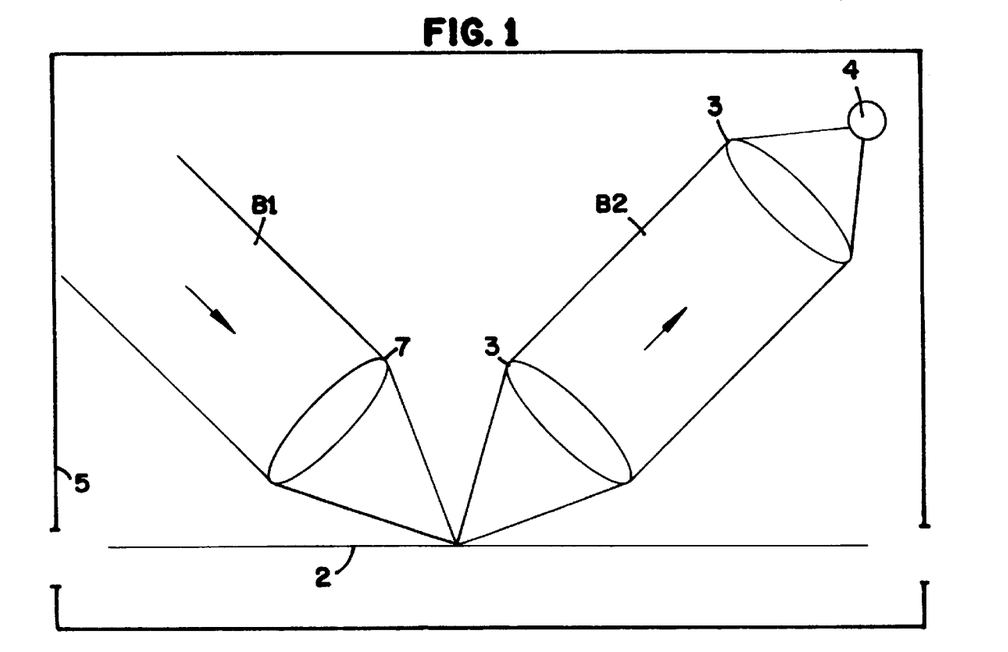
FIG. 1 presents a diagram representing diffuse reflection measurement.

In FIG. 1, a parallel measuring beam B1 is directed via a lens 1 obliquely to a paper sample 2 to be measured, from which a parallel reflected beam B2 is directed via a lens system 3 to a detector 4. The measuring beam B1 may consist of rays of light having different wavelengths, e.g. 2–12 μm. The detector 4 determines the intensity of beam B2 as a function of different beam wavelength λ. The paper 2 may be stationary, e.g. during laboratory measurement, or it may be moving, e.g. in a paper machine. A paper machine 5 is schematically shown. A roller 6 is schematically shown under the paper 2. The techniques of applying a measuring light beam B1 and detecting the intensity of the reflected beam B2 as a function of the wavelength λ of the light are known in themselves and will not be described here in detail. Measurement in the MIR range can be advantageously implemented using specular optics, which is known itself and will not be described here in detail.

Figure 2:
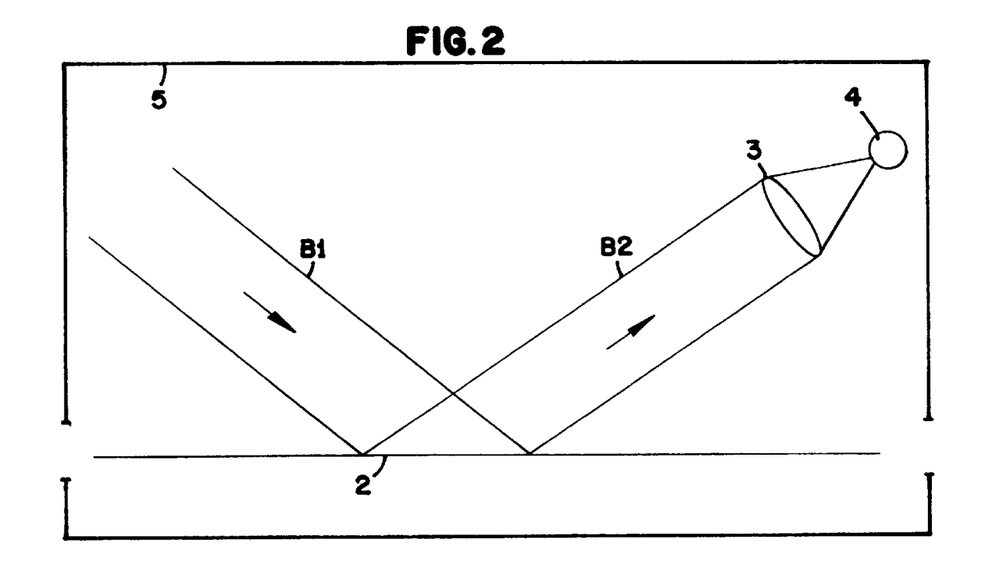
FIG. 2 presents a diagram representing specular reflection measurement.

FIG. 2 presents a diagram of specular reflection measurement. The incident beam B1 is directed e.g. as a beam of parallel rays at an oblique angle to the paper 2 and the beam B2 of parallel rays reflected from the paper is detected in a manner known in itself by means of a lens system 3 and a detector 4, the intensity of the reflected beam being measured as a function of the wavelength λ of the light. A paper coating machine 7 is schematically shown. A metal plate 8 is schematically shown under the paper 2.

Figure 3:
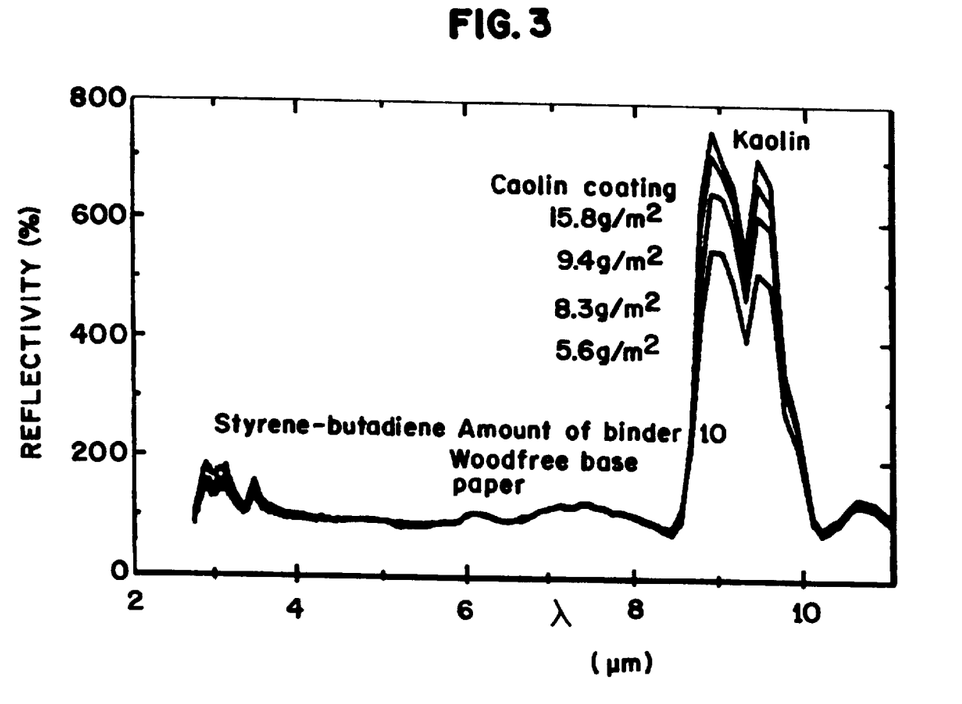
FIG. 3 and 4 represent reflectivity (%), i.e. light intensity measured as a function of wavelength with a wavelength of about 2–11 μm.
Figure 4:
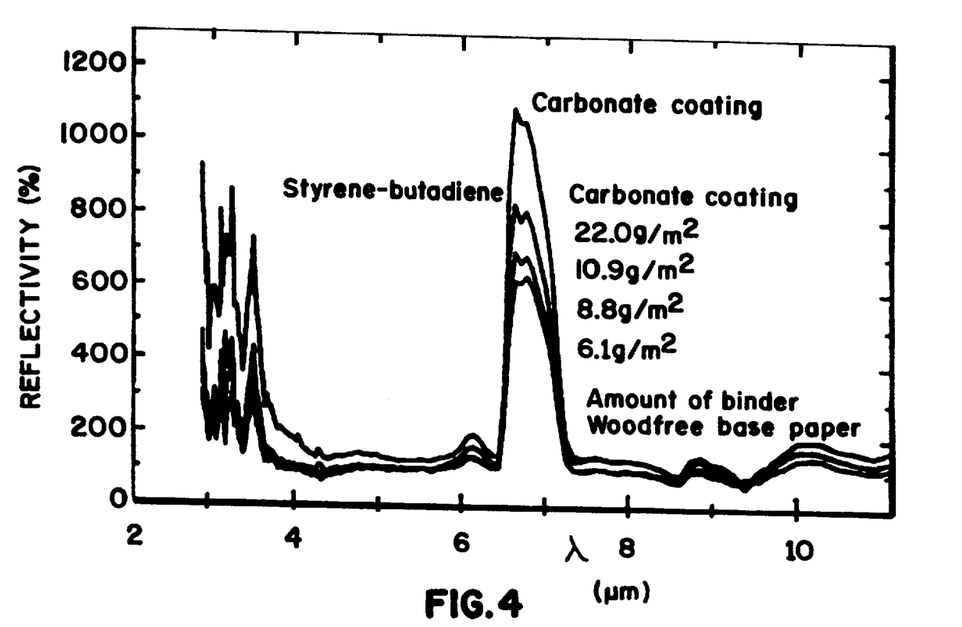

FIGS. 3–4 present graphs showing the results of a specular reflection measurement carried out in the manner illustrated by FIG. 2, compared with the reflectivity of the base paper, the reflection spectrum of kaolin-coated paper (FIG. 3) and carbonate-coated paper (FIG. 4) being shown in relation to the base paper spectrum. A peak for kaolin is seen in FIG. 3 at wavelength 8.5–10 μm and a carbonate peak in FIG. 4 at wavelength 6.5–7 μm. A peak for styrene-butadiene, which is used as a binder, is seen around 3 μm (FIG. 4). The peaks are very pronounced, because at the wavelengths of the peaks caused by the pigments the reflectivity of the coated paper is 5–11 times higher than the reflectivity of the base paper.

To determine the usability of the measuring procedure, a series of measurements of the amount of coating on kaolin-coated and carbonate-coated paper were carried out. During the measurements it was observed that the measurement peak response increased so heavily with the increase of the measuring angle used in the measurement of the amount of coating that a selection had to be made between measurement dynamics and depth of penetration. As a compromise, the measurements were carried out as diffused reflection measurements, in which, due to a good signal-to-noise ratio, better calibration results were achieved than in specular reflection measurement. Besides, diffusion measurement is not as distance-sensitive as specular reflection measurement.

Figure 5:
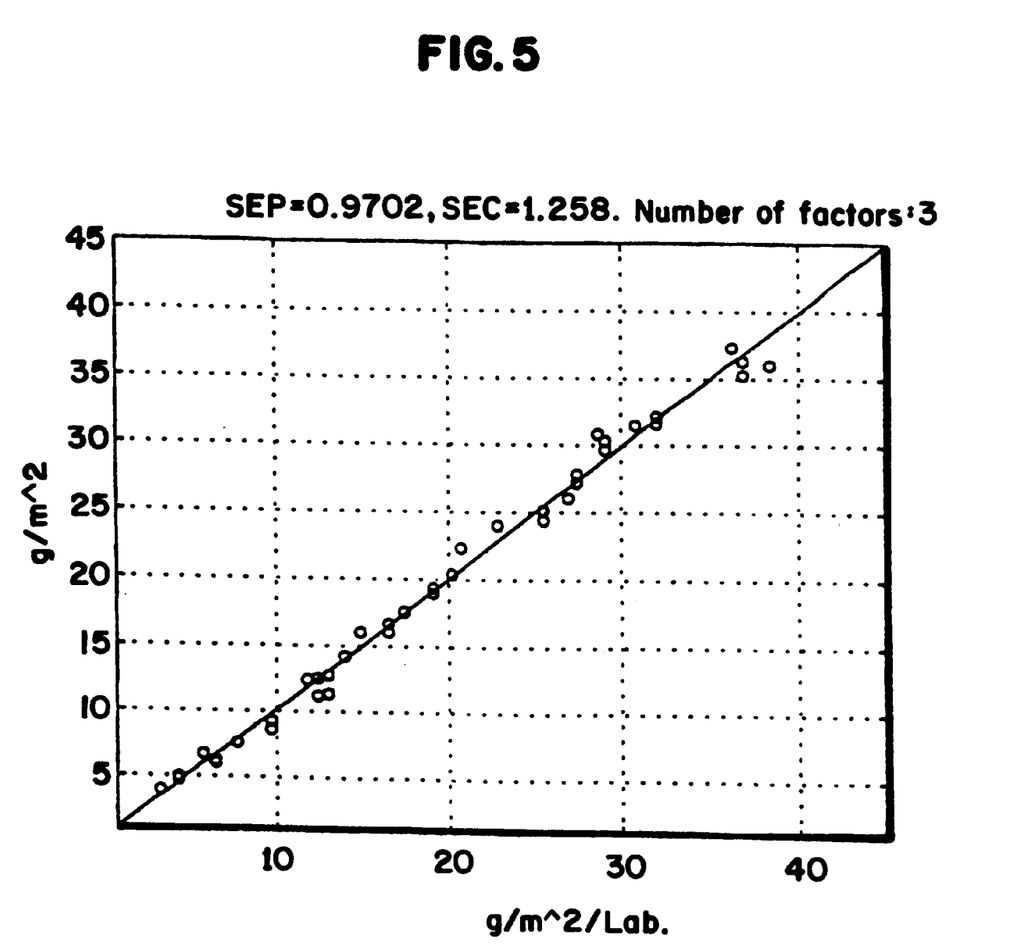
FIG. 5–9 present graphs representing amounts of coating determined by the method of the invention as functions of amounts of coating determined via laboratory measurements.
Figure 6:
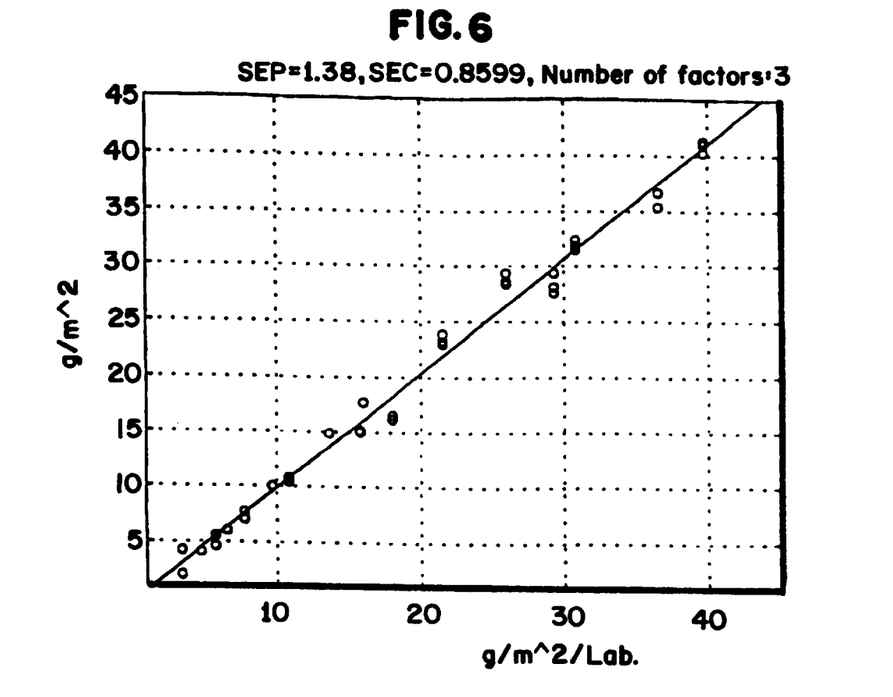
Figure 7:
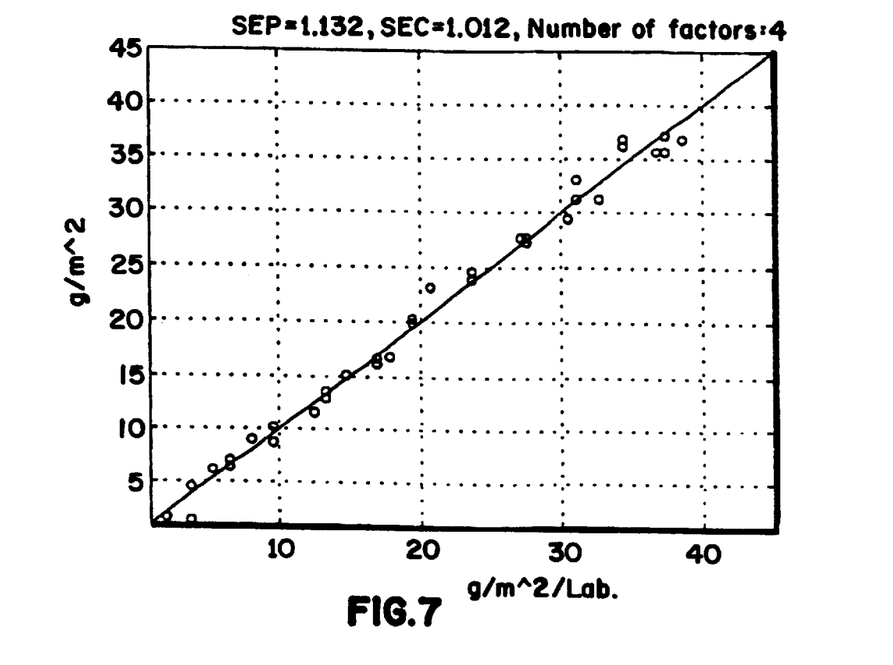
Figure 8:
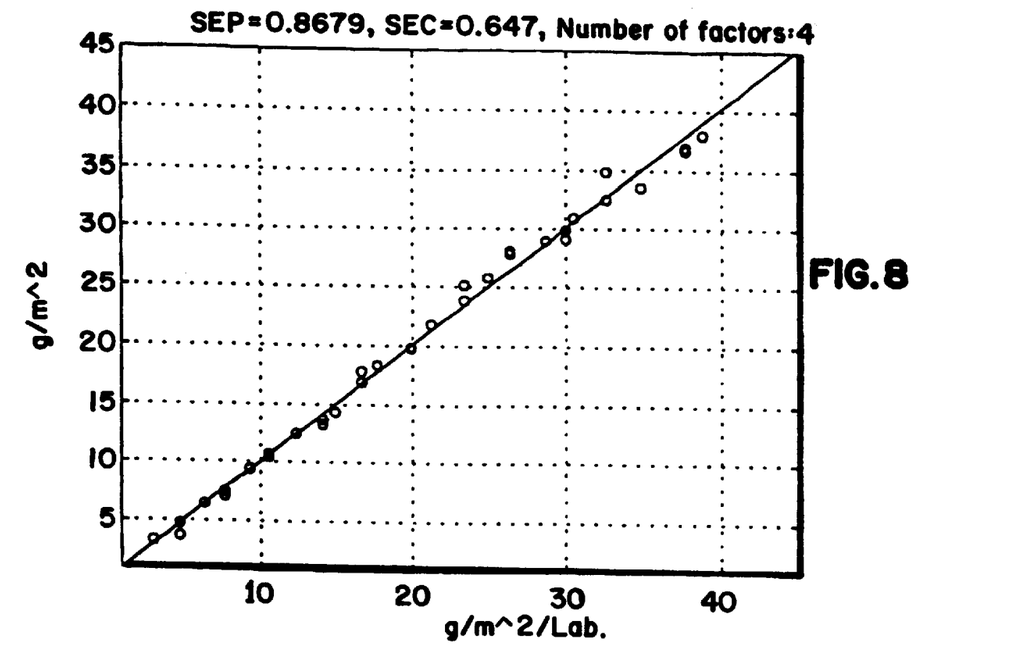
Figure 9:
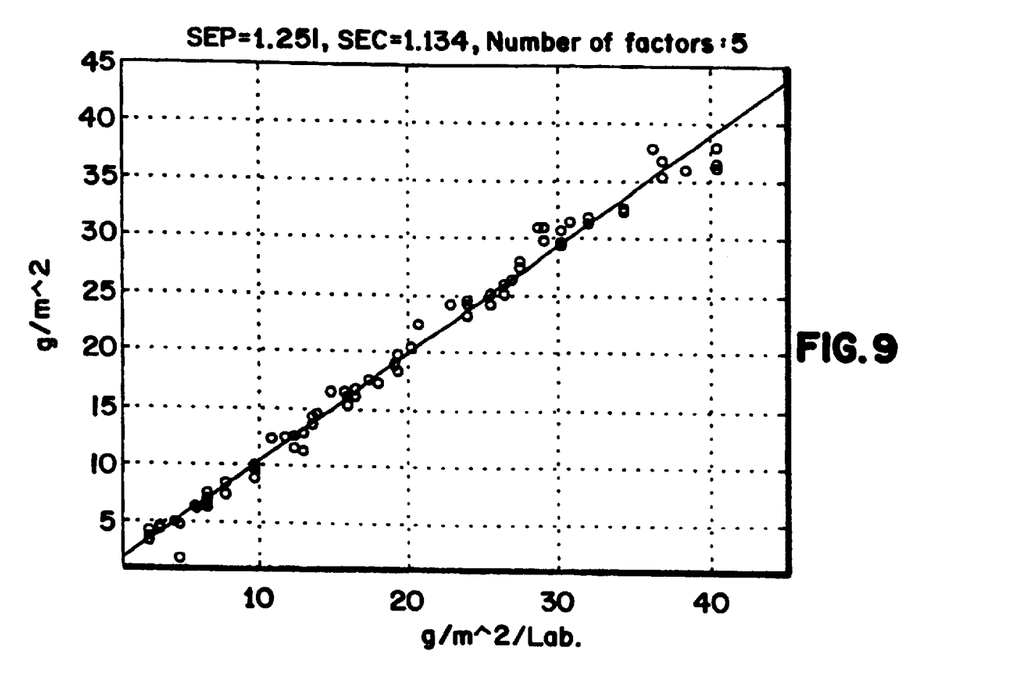

The measurements of the amounts of coating were carried out using a Bomem FTIR spectrometer with a commercial diffuse reflection accessory (Harrick, The Praying Mantis). During the measurements, the sample was moved over the measurement sample aperture by means of an electric motor, the measuring spot having a diameter of about 3 mm. For the paper samples measured, corresponding component determinations were carried out by laboratory measuring methods. In FIGS. 5–9, the amounts of components determined using the procedure of the invention are shown on the Y-axis while the corresponding amounts of components determined by laboratory methods are shown on the X-axis. FIG. 5 represents the measurement of kaolin coating on wood-containing base paper, FIG. 6 the measurement of kaolin coating on woodfree base paper, FIG. 7 the measurement of carbonate coating on wood-containing base paper, FIG. 8 the measurement of carbonate/kaolin coating on wood-containing base paper and FIG. 9 the measurement of kaolin coating on woodfree base paper. From the results were calculated the standard deviation (SEC) of the determinations carried out by the method of the invention and the standard deviation (SEC) of the determinations carried out by laboratory methods; the number of factors represents the number of variables used in the determinations carried out by laboratory methods.

Figure 10:
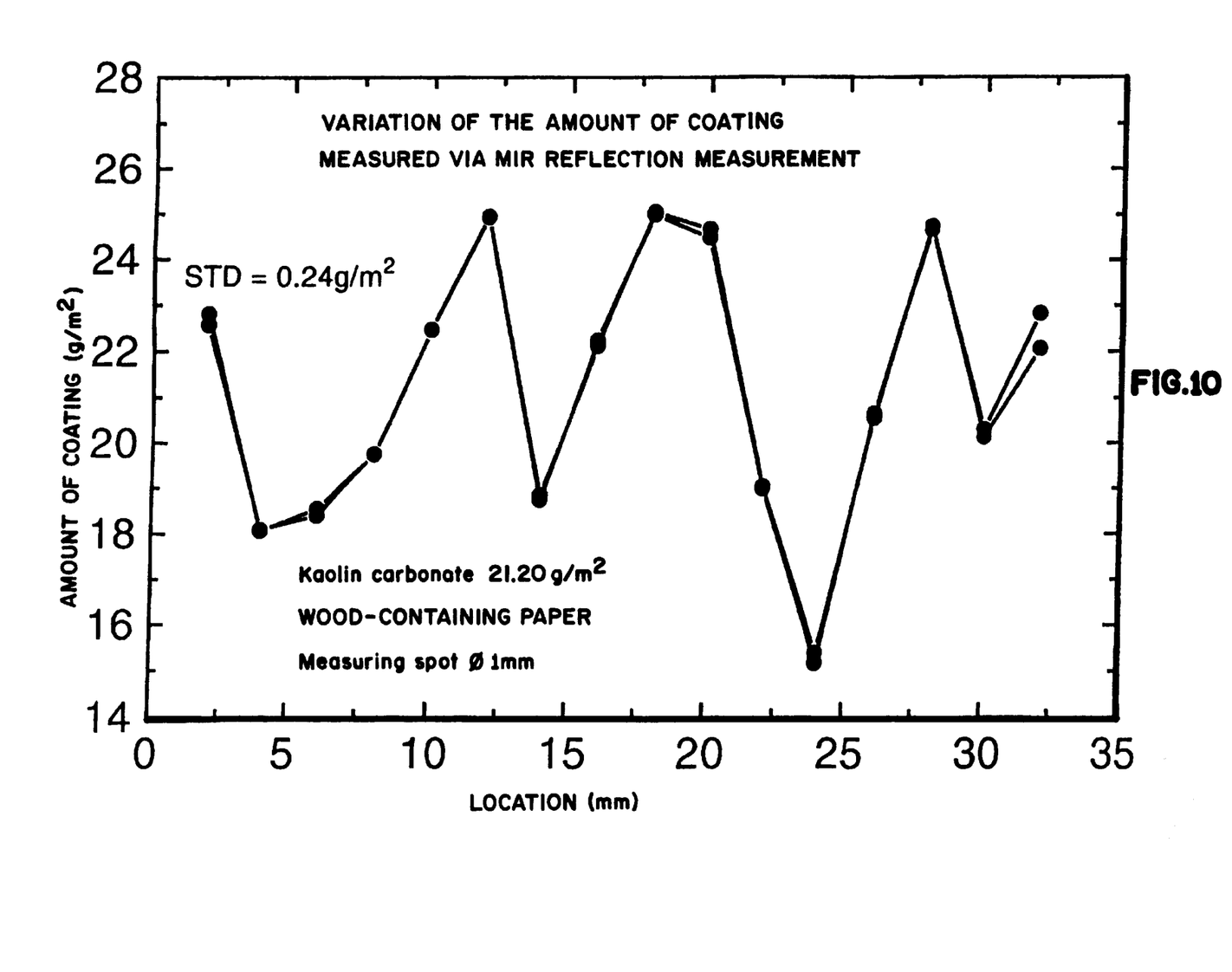
FIG. 10 presents a graph representing small-scale variation in the amount of coating as measured by the method of the invention from a measuring area of 1 mm².

FIG. 10 illustrates the variation in small-scale amount of coating and the deviation in the measurement of the amount of coating when the measurement was repeated twice on the same spots with a diameter of 1 mm.

Figure 11:
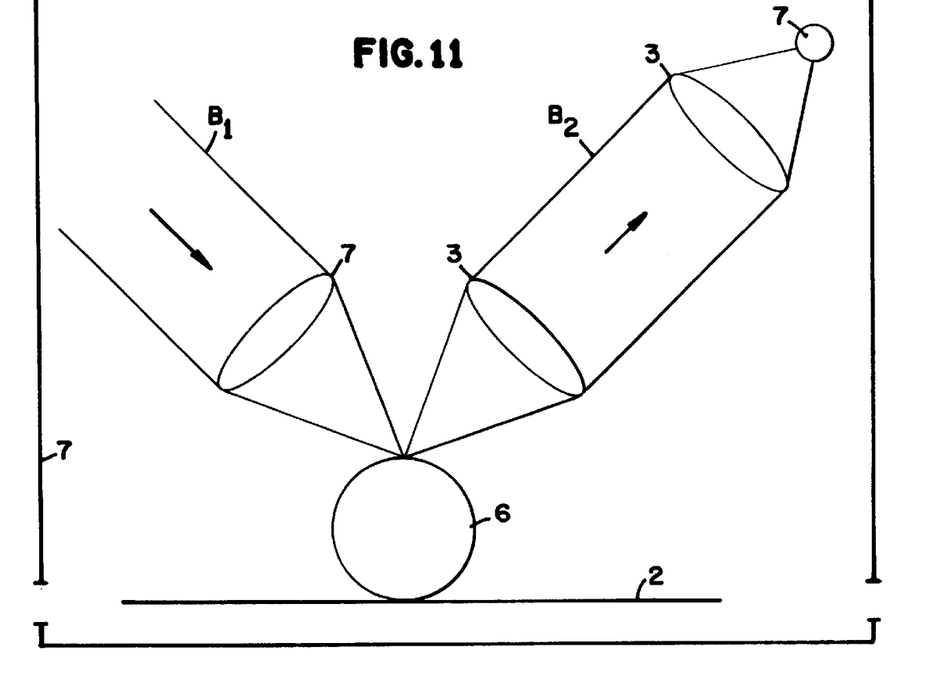
FIG. 11 schematically shows a roller of a paper coating machine.

FIG. 11 schematically shows a roller 6 of a paper coating machine 7.

Figure 12:
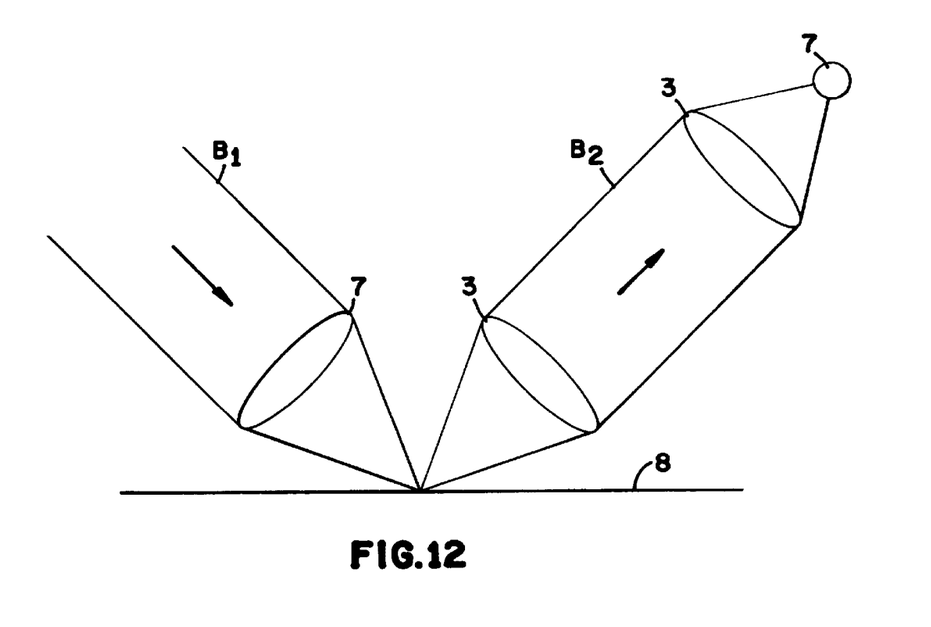
FIG. 12 schematically shows a metal plate carrying the coating whose components are to be measured.

FIG. 12 schematically shows a metal plate 8 carrying the coating whose components are to be measured.

The embodiment examples are intended to visualize the invention without limiting it in any way.

We claim:

1. Method for measuring the components of a coating on a moving base material by an infrared measuring technique, wherein an amount of calcium carbonate in the coating is determined via reflection measurement in a wavelength range of 2.5–12 μm.

2. Method according to claim 1, wherein also an amount of kaolin in the coating is determined in a wavelength range of 8–11 μm.

3. Method according to claim 2, wherein the amount of kaolin is determined in a wavelength range of 8.5–10 μm.

4. Method according to claim 1, wherein the amount of calcium carbonate in the coating is determined in a wavelength range of 5.5–8 μm.

5. Method according to claim 4, wherein the amount of calcium carbonate is determined in a wavelength range of 6.2–7.3 μm.

6. Method according to claim 1, wherein also a reflection spectrum is measured in a wavelength range of 2.5–12 μm.

7. Method according to claim 1, wherein the amount of calcium carbonate is measured in a measurement area of 0.1–100 mm$^2$.

8. Method according to claim 1, wherein the reflection measurement is implemented using specular reflection measurement.

9. Method according to claim 1, wherein the reflection measurement is implemented using diffuse reflection measurement.

10. Method according to claim 1, wherein the moving base material carrying the coating whose components are to be measured is paper or cardboard.

11. Method according to claim 1, wherein the moving base material carrying the coating whose components are to be measured is a roller in a paper coating machine.

12. Method according to claim 1, wherein the moving base material carrying the coating whose components are to be measured is a roller in a paper machine.

13. Method according to claim 1, wherein the moving base material carrying the coating whose components are to be measured is a metal plate.

* * * * *

UNITED STATES PATENT AND TRADEMARK OFFICE
CERTIFICATE OF CORRECTION

PATENT NO. : 5,914,490
DATED : June 22, 1999
INVENTOR(S) : Sumén et al.

It is certified that error appears in the above-identified patent and that said Letters Patent is hereby corrected as shown below:

Title page,
Item [73], Assignee, please replace "Valmet/Automatic, Inc., Helsinki, Finland" with -- Valmet Automation, Inc., Helsinki, Finland --.

Signed and Sealed this

Nineteenth Day of February, 2002

Attest:

Attesting Officer

JAMES E. ROGAN
Director of the United States Patent and Trademark Office